(12) United States Patent
Bing (10) Patent No.: US 6,538,033 B2
(45) Date of Patent: Mar. 25, 2003

(54) NITRIC OXIDE DONOR COMPOUNDS

(75) Inventor: Richard J. Bing, La Canada, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 0 days.

(21) Appl. No.: 09/942,180

(22) Filed: Aug. 29, 2001

(65) Prior Publication Data

US 2002/0032232 A1 Mar. 14, 2002

Related U.S. Application Data (60) Provisional application No. 60/228,669, filed on Aug. 29, 2000.

(51) Int. Cl.⁷ .............................................. C07C 205/45
(52) U.S. Cl. ........................................ 514/645; 558/482
(58) Field of Search ........................... 558/482; 514/645

(56) References Cited

U.S. PATENT DOCUMENTS

| | | |
|---|---|---|
| 5,366,992 A | 11/1994 | Sala, et al. |
| 5,589,490 A | 12/1996 | Sala, et al. |
| 5,621,000 A | 4/1997 | Arena, et al. |
| 5,859,053 A | 1/1999 | Lesur, et al. |
| 6,040,341 A * | 3/2000 | Del Soldato et al. ....... 514/509 |

FOREIGN PATENT DOCUMENTS

| | | |
|---|---|---|
| EP | 0251039 B1 | 9/1991 |
| WO | WO94/12463 | 6/1994 |

OTHER PUBLICATIONS

Bing et al. The Pharmacology of a New Nitric Oxide Donor: B–NOD, Biochemeical and Biophysiscal Research Communications, vol. 275 #2, pp. 350–353, Academic Press, Aug. 28, 2000.*

KITA, Y., et al., *FR144420, A Novel, Slow, Nitric Oxide–Releasing Agent,* European Journal of Pharmacology, 1995, pp. 125–129, vol. 275, Elsevier Science B.V.

* cited by examiner

*Primary Examiner*—Joseph K. McKane
*Assistant Examiner*—Rebecca Anderson
(74) *Attorney, Agent, or Firm*—Christie, Parker & Hale, LLP (57) ABSTRACT

Nitric oxide donor compounds of the formula:

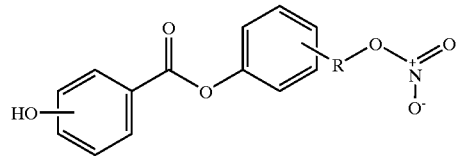

are provided. In the formula, R is $(CH_2)_n$, wherein n ranges from 1 to 8 and wherein each hydrogen atom on the alkylene group and on the phenyl groups can optionally be replaced by a substituent selected from the group consisting of alkyl, cycloalkyl, heterocycloalkyl, aryl, heteroaryl, halo, and hydroxy groups. A particularly preferred compound is 1,3-(nitrooxymethyl)phenyl 2-hydroxybenzoate. The compounds are useful for treating and preventing various conditions, including coronary artery disease.

40 Claims, 5 Drawing Sheets

NITRIC OXIDE DONOR COMPOUNDS

CROSS-REFERENCE TO RELATED APPLICATION

This application claims the benefit of U.S. Provisional Patent Application No. 60/228,669, filed Aug. 29, 2000, the entire disclosure of which is incorporated herein by reference.

BACKGROUND OF THE INVENTION

Nitric oxide donor compounds (NO donors) have been used for many years in the treatment of various clinical conditions, particularly coronary artery disease. (Harrison, D. G. and Bates, J. N. (1993) The nitrovasodilators: new ideas about old drugs. *Circulation* 87, 1461–1467.) They cause vasodilation, inhibit platelet aggregation, diminish myocardial contractile force and counteract thromboxane $A_2$. (Bing, R. J., Yamamoto, T., Yamamoto, M., Kakar, R. and Cohen, A. (1999) New look at myocardial infarction: toward a better aspirin. *Cardiovasc Res* 43, 25–31.) The NO releasing ability of these compounds is due to nitrate functionality within the molecule. A nitroso functional group is present in all NO donor compounds. Some of these compounds need biochemical conversion, or biotransformation, of the nitrate group to NO. (Torfgard, K. E. and Ahlner, J. (1994) Mechanisms of action of nitrates. *Cardiovasc Drugs Ther* 8, 701–717.) The duration of their activity in vivo also varies. The oxidation products of NO are $NO_2^-$ and $NO_3^-$, collectively referred to as $NO_x$. Many of the existing NO donors must be administered intravenously, which results in rapid onset of decreasing blood pressure accompanied by unwanted side effects. Their effect does not extend beyond the period of infusion. Another undesirable side effect of some NO donors includes an increase in heart rate. A need exists for an NO donor compound to treat disease that does not affect blood pressure or heart rate.

SUMMARY OF THE INVENTION

The invention is directed to a novel genus of compounds that are particularly useful as nitric oxide donors, as well as to methods of treatment using these compounds. In one embodiment, the invention is directed to a composition comprising a compound of the formula:

wherein R is $(CH_2)_n$, wherein n ranges from 1 to 8 and wherein each hydrogen atom on the alkylene group and on the phenyl groups are optionally replaced by a substituent selected from the group consisting of alkyl, cycloalkyl, heterocycloalkyl, aryl, heteroaryl, halo, and hydroxy groups. Preferably the composition comprises the compound 3-(nitrooxymethyl)phenyl 2-hydroxybenzoate, referred to as B-NOD, of the formula:

The compounds of the invention are useful as nitric oxide donor compounds that can be administered orally and that do not affect blood pressure or heart rate. It has been discovered that B-NOD generates NO in vivo and in vitro in a concentration- or dose-dependent manner. It is likely that NO release is enzymatically catalyzed, consistent with the findings that in vitro NO release is augmented by the presence of living cells, including blood platelets.

The invention is also directed to methods of treatment utilizing the above compounds. In one embodiment, the invention is directed to a method for treating coronary artery disease comprising administering a pharmaceutically-acceptable amount of a composition as described above to a patient in need thereof. These compositions are particularly useful for treating coronary artery disease following myocardial infarction because they influence contractility and metabolic function of the infarcted heart and reduce infarct size. In addition, these compounds are useful for counteracting thromboxane, inhibiting platelet activation, stimulating pro stanoids through activation of cyclooxygenase, reducing myocardial contractility, attenuating inotropic response, reducing cardiac lactate accumulation by forming cGMP, dilating coronary arteries, and suppressing ventricular fibrillation. These compounds may also be useful for treating or preventing strokes or embolism.

Notably, B-NOD is active for up to seven hours following administration. B-NOD inhibits platelet aggregation through stimulation of guanalate cyclase, increases cyclic guanosine monophosphate (cGMP) production in a dose-dependent manner, causes the release of prostanoids, causes vasodilation, affects angiogenesis, and produces oxygen free radicals.

B-NOD has significant advantages over other NO donor compounds. Compared to nitroglycerin (American Radiolabeled Chemicals, Inc. St. Louis, Mo.), B-NOD releases NO for much longer periods, does not cause a decrease in blood pressure, and is only a partial pro-drug because it releases NO only after biotransformation of the nitrite group to NO. (Robertson, R. M. and Robertson, D. (1996) in The pharmacological basis of therapeutics (Goodman and Gilman, eds.), 9th ed., pp. 759–779, McGraw-Hill, New York.) B-NOD has longer action than the NO donor FR144420, (+/-)—N—[(E)-4-Ethyl-3-[(Z)-hydroxyimino]-5-nitro-3-hexen-1-yl]-3-pyridinecarboxamide, (Fujisawa Pharmaceutical Co., Osaka, Japan), and does not affect blood pressure. (Kita, Y., Ohkubo, K., Hirasawa, Y., Katayama, Y., Ohno, M., Nishino, S., Kato, M. and Yoshida, K. (1995) FR144420, a novel, slow, nitric oxide-releasing agent. *Eur J Pharmacol* 275,125–130.) Compared to B-NOD, the NO-aspirin compound NCX 4016,2-acetoxybenzoate-2(1 nitroxy-methyl)-phenylester (AstraZeneca, Södertälje, Sweden), of the formula:

has aspirin-like qualities that are undesirable in some circumstances, namely, inhibition of the isoenzymes cyclooxygenase-1 and cyclooxygenase-2 because of its aspirin moiety. (Cuzzolin L., Adami A., Degan M., Crivellente F., Bonapace S., Minuz P., Benoni G. Effect of single and repeated of anew nitroderivative of acetylsalicylic acid on platelet $TXA_2$ production in rats. Life Sci 38:207–210, 1996.)

B-NOD does not cause a decrease in heart rate or an increase in blood pressure after administration, significant advantages over other NO donor compounds. B-NOD can be administered orally, unlike other NO donor compounds that must be administered intravenously, such as sodium nitroprusside (SNP) (Bates, J. N., Baker, M. T., Guerra, R., Jr. and G., H. D. (1991) Nitric oxide generation from nitroprusside by vascular tissue. *Biochem Pharmacol* 42(Suppl), S157–S165), SIN-1 (Arkonac, B. M., Kersten, J. R., Wynsen, J. C., Nijhawan, N. and Warltier, D. C. (1996) Differential hemodynamic effects of the nitric oxide donor pirsidomine in comparison to SIN-1, nitroprusside and nitroglycerin. *Pharmacology* 52, 92–100) and diethylenetriamine/nitric oxide (DETA/NO) (Takano, H., Tang, X. -L., Qiu, Y., Guo, Y., French, B. A. and Bolli, R. (1998) Nitric oxide donors induce late preconditioning against myocardial stunning and infarction in conscious rabbits via an antioxidant-sensitive mechanism. *Circ Res* 83, 73–84) (all available from ICN Pharmaceuticals, Inc., Costa Mesa, Calif.).

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The invention is directed to a novel genus of compounds that are particularly useful as nitric oxide donors, as well as to compositions containing these compounds and methods of using these compounds. The compounds have the formula:

wherein R is $(CH_2)_n$, wherein n ranges from 1 to 8. Each hydrogen atom on the alkylene group, which is adjacent the nitro group, and each hydrogen atom on the two phenyl groups is optionally replaced by a substituent selected from the group consisting of alkyl, cycloalkyl, heterocycloalkyl, aryl, heteroaryl, halo, and hydroxy groups. The essential features of these compounds are their nitric oxide-releasing group and the absence of a methyl ester group at position 2, which is responsible for aspirin-like qualities.

As used in the present application, the following definitions apply, unless otherwise indicated:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, cyclopropyl, cyclobutyl, cyclopentyl, cyclopentenyl, cyclohexyl, cyclohexenyl, cycloheptyl, cyclooctyl, bicyclo[2.2.1.]heptyl, bicyclo[2.2.1.]hept-2-en-5-yl, bicyclo[2.2.2]octyl, bicyclo[3.2.1.]nonyl, bicyclo[4.3.0]nonyl, bicyclo[4.4.0]decyl, indan-1-yl, indan-2-yl, tetralin-1-yl, tetralin-2-yl, adamantyl, and the like.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl,azabicylo[3.3.1]nonyl, azabicylo[4.3.0]nonyl,oxabicylo[2.2.heptyl, 1,5,9-triazacyclododecyl, and the like.

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, fluoren-2-yl, indan-5-yl, and the like.

A "heteroaryl group" is intended to mean an aromatic monovalent monocyclic, bicyclic, ortricyciic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, pyrrolyl, imidazolyl, pyrazolyl, furyl, thienyl, thiazolyl, oxazolyl, isoxazolyl, isothiazolyl, oxadiazolyl, triazolyl, tetrazolyl, pyrazinyl, pyridyl, pyrimidyl, pyridazinyl, indolyl, isoindolyl, benzimidazolyl, benzofuryl, isobenzofuryl, benzothienyl, quinolyl, isoquinolyl, phthalazinyl, carbazolyl, purinyl, pteridinyl, acridinyl, phenanthrolinyl, phenoxazinyl, phenothiazinyl, and the like.

The term "suitable substituent" is intended to mean any of the substituents recognizable to those skilled in the art as not adversely affecting the inhibitory activity of the inventive compounds. Illustrative examples of suitable substituents include, but are not limited to, oxo groups, hydroxy groups, halo groups, cyano groups, nitro groups, amino groups, alkyl groups, cycloalkyl groups, heterocycloalkyl groups, aryl groups, and heteroaryl groups.

A "hydroxy group" is intended to mean the radical —OH.

An "oxo group" is intended to mean the divalent radical =O.

A "halo group" is intended to mean any of the radicals —F, —Cl, —Br, or —I.

A "cyano group" is intended to mean the radical —CN.

A "nitro group" is intended to mean the radical —$NO_2$.

An "amino group" is intended to mean the radical —$NH_2$.

In a particularly preferred embodiment, the invention is directed to a compound of the formula:

wherein R is $(CH_2)_n$, wherein n ranges from 1 to 8. Each hydrogen atom on the alkylene group, which is adjacent the nitro group, and each hydrogen atom on the two phenyl groups is optionally replaced by a substituent selected from the group consisting of alkyl, cycloalkyl, heterocycloalkyl, aryl, heteroaryl, halo, and hydroxy groups.

The inventive compounds may be administered as a pharmaceutical composition in any suitable pharmaceutical form recognizable to the skilled artisan. Suitable pharmaceutical forms include, but are not limited to, solid, semisolid, liquid or lyophilized formulations, such as tablets, powders, capsules, suppositories, suspensions and aerosols. Preferably the pharmaceutical form is a tablet or capsule for oral administration. The pharmaceutical composition may also include suitable excipients, diluents, vehicles and carriers as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling, and dissolving the ingredients as appropriate, to give the desired products for oral, parenteral, topical, intravaginal, intranasal, intrabronchial, intraocular, intraaural and/or rectal administration. Illustrative examples of such methods include those described in Remington's Pharmaceutical Sciences, 18th edition (1990).

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

The compositions of the invention may be administered by any suitable means, for example by intravenous, intramuscular, intraperitoneal, transmucosal, transdermal, or oral means. The compositions are preferably administered orally. In accordance with the present invention, the compositions are preferably administered at a dose ranging from about 1 to about 500 mg/kg/day, more preferably at a dose ranging from about 5 to about 400 mg/kg/day, even more preferably at a dose ranging from about 100 to about 200 mg/kg/day, still more preferably at a dose of about 150 mg/kg/day. The compositions are preferably administered in a frequency that ranges from about four times per day to once a week, more preferably once or twice a day. Treatment comprising these compositions can be short term or long term Short term treatment ranges from one day (or one single use) to about one month. Long term treatment ranges from about one month to over two years or chronic/maintenance administration.

The compounds of the invention release NO in vivo and in vitro via enzymatic cleaveage. NO has been found to counteract thromboxane, inhibit platelet activation, stimulate pro stanoids through activation of cyclooxygenase, influence contractility and metabolic function of the infarcted heart, reduce myocardial contractility, attenuate inotropic response, form cGMP which reduces cardiac lactate accumulation, dilate coronary arteries, supress ventricular fibrillation and reduce infarct size.

The inventive compounds can be prepared by employing the techniques available in the art using staring materials that are readily available. An exemplary method of preparing the inventive compounds is set forth below. Specifically, B-NOD can be prepared in five steps by the following synthetic scheme and the steps described below.

B-NOD

Unless otherwise specified, all commercial chemicals were purchased from the Sigma-Aldrich Co. and used without further purification. Anhydrous tetrahydrofuran (THF) and diethylether ($Et_2O$) were obtained by drying through a dried alumina column. All reactions were performed under dry argon gas unless otherwise noted. Analytical thin-layer chromatography was performed on 0.25 μm silica gel 60 $F_{254}$ plates (E. Merck). Flash column chromatography was performed using the indicated solvent with 40–63 μm silica gel 60 (E. Merck).

Step 1: Synthesis of Bis(t-butyldimethylsilyl) ether of 3-hydroxybenzyl alcohol (Compound 2)

To a solution of 3-hydroxybenzyl alcohol (Compound 1) (3.0 g, 0.024 mol) and t-butyldimethylsilyl chloride (TBSCl) (11 g, 0.072 mol) in dimethyl formamide (DMF) (120 ml) was added imidazole (4.9 g, 0.072 mol). The reaction mixture was stirred at room temperature (RT) under argon for 18 hours. Then the reaction mixture was diluted with ethylacetate (EtOAc) (200 ml) and washed with water (5×300 ml), aqueous saturated sodium bicarbonate ($NaHCO_3$) (2×200 ml), and brine (1×200 ml). The resulting organic solution was dried over anhydrous sodium sulfate ($Na_2SO_4$). The crude product obtained upon concentration of the organic solution was purified by column chromatography (elution solvent: 2% EtOAc in hexanes) to produce 8.4 g of Compound 2 in 100% yield.

Step 2: Synthesis of 3-(t-Butyldimethylsilyloxymethyl) phenol (Compound 3)

To a solution of Compound 2 in THF (120 ml), was added a solution of tetrabutylammonium fluoride (TBAF) (24 ml, 1 M in THF) at 0° C. The reaction mixture was then stirred at 0° C. under argon for 20 minutes. Then the reaction mixture was treated with aqueous saturated ammonium chloride ($NH_4Cl$) (100 ml), and the resulting layers were separated. The aqueous layer was extracted with $Et_2O$ (3×60 ml). All of the organic layers were combined and washed with aqueous saturated $NH_4Cl$ (1×10 ml), brine (1×10 ml), and dried over anhydrous $Na_2SO_4$. The crude product obtained upon concentration was purified by filteration over a pad of silica gel (elution solvent: 20% EtOAc in hexanes) to produce 5.6 g of Compound 3 in 98% yield.

Step 3: Synthesis of 3-(t-Butyldimethylsilyloxymethyl) phenyl 2-(acetyloxy)benzoate (Compound 5)

To a solution of Compound 3 in $Et_2O$ (120 ml) were added acetylsalicyloyl chloride (Compound 4) (5.9 g, 0.028 mol) and triethylamine ($Et_3N$) (6.6 ml, 0.047 mol) in sequence at RT. The reaction mixture was stirred at RT under argon for 3 days. The reaction mixture was diluted with EtOAc (100 ml) and washed with aqueous saturated $NaHCO_3$ (3×100 ml), brine (1×100 ml), and dried over anhydrous $Na_2SO_4$. The crude product obtained upon concentration was purified by column chromatography (elution solvent: 5% EtOAc in hexanes) to produce 9.4 g of Compound 5 in 100% yield.

Step 4: Synthesis of 3-(Hydroxymethyl)phenyl 2-hydroxybenzoate (Compound 6)

To a solution of Compound 5 (9.4 g, 0.024 mol) in THF (120 ml) was added a solution of hydrochloric acid (HCl)

(100 ml, 6 N HCl in water) at RT. The reaction mixture was stirred at RT for 2 days. Then, the reaction mixture was mixed with EtOAc (300 ml) and the resulting layers were separated. The organic layer was washed with aqueous saturated $NaHCO_3$ (3×100 ml) and brine (1×100 ml). The aqueous layer was neutralized to pH 7 with aqueous saturated $NaHCO_3$, and extracted with EtOAc (2×100 ml). These EtOAc extracts were combined and washed with brine (1×100 ml). Then, all the organic layers were combined and dried over anhydrous $Na_2SO_4$. The crude product obtained upon concentration was purified by column chromatography (elution solvent: 30% EtOAc in hexanes) to yield 5.0 g of Compound 6 in 87% yield.

Step 5: Synthesis of 3-(Nitrooxymethyl)phenyl 2-hydroxybenzoate (B-NOD)

Triphenylphosphine ($PPh_3$) (5.4 g, 0.020 mol) and Compound 6 (5.0 g, 0.020 mol) were dissolved in a mixture of acetonitrile ($CH_3CN$) (120 ml) and methylene chloride ($CH_2Cl_2$) (40 ml). The resulting colorless clear solution was cooled to −35° C. The reaction mixture was treated with N-bromosuccinimide (NBS) (3.8 g, 0.021 mol) and was stirred at −35° C. under argon for 30 minutes. The reaction mixture was treated with silver nitrate ($AgNO_3$) (4.2 g, 0.025 mol) and the cooling bath was removed. Stirring continued at RT under argon for 3 days. Then, the reaction mixture was filtered over a pad of silica gel, diluted with EtOAc (100 ml), washed with water (3×100 ml), brine (1×100 ml), and dried over anhydrous $Na_2SO_4$. The crude product obtained upon concentration was purified by column chromatography (elution solvent: 10% EtOAc in hexanes) to yield 4.3 g of B-NOD in 73% yield.

EXAMPLES

Example 1

Nitric Oxide Generation In Vitro

Venous blood was collected from healthy volunteers who had not previously been taking any drugs for at least two weeks; EDTA was used as an anticoagulant. Washed platelets were prepared as described in Radomski, M. and Moncada, S. (1983) An improved method for washing of human platelets with prostacyclin. *Thromb Res* 83,383–389, the disclosure of which is incorporated herein by reference, with some modifications. In brief, blood was centrifuged for 10 minutes at 200 g, and the resultant platelet rich plasma was removed. It was recentrifuged at 500 g for 10 minutes. The supernatant was discarded and the pellet was resuspended in Tyrode's solution. Platelet concentration was adjusted to $2 \times 10^8$ platelets/ml using a Coulter Counter (Model ZBI, Beckman-Coulter, Fullerton, Calif.). 400 µl aliquots of the platelets were incubated in the presence of B-NOD (10, 100 or 1000 µM) or methanol for 10 minutes. To determine whether B-NOD could spontaneously release nitric oxide, the drug was also incubated at 37° C. in the absence of washed platelets. Incubations were terminated by centrifugation at 1000 g.

The supernatant was analyzed for nitric oxide generation by chemiluminescence. Samples were treated with the enzyme Aspergillus nitrate reductase. For analysis of plasma $NO_x$, 25 µl of nitrate reductase (2 U/ml) was added to 2.5 µl of flavin adenine dinucleotide (120 mM), 2.5 µl of NADPH (144 mM), 20 µl of phosphate buffered saline (10 mM, pH =7.4) and 25 µl of sample for a final volume of 75 µl. All samples were incubated at 37° C. for 1 hour. After incubation, 30 µl samples were injected into a reaction vessel. Chemiluminescence was measured using a reducing system consisting of a ferrocene derivative dissolved in acetonitrile containing 1% perchloric acid, as described in Termin, A., Hoffmann, M. and Bing, R. J. (1992) A simplified method for the determination of nitric oxide in biological solutions. *Life Sci* 51, 1621–1629, the disclosure of which is incorporated herein by reference. Under this condition, $NO_2$ in the injected samples was reduced to NO and detected by chemiluminescence with the NO-analyzer (270 B, Sievers Res. Inc., Boulder, Colo.). In brief, blood was centrifuged for 10 minutes at 200 g, and the resultant platelet rich plasma was removed. It was recentrifuged at 500 g for 10 minutes. The supernatant was discarded and the pellet was resuspended in Tyrode's solution. Platelet concentration was adjusted to $2 \times 10^8$ platelets/ml using a Coulter Counter (Model ZBI, Beckman-Coulter, Fullerton, Calif.). Aliquots (400 l) of the platelets were incubated in the presence of B-NOD (10, 100 or 1000 µM) or methanol for 10 minutes. To determine whether B-NOD can spontaneously release nitric oxide, the drug was also incubated at 37° C. in the absence of washed platelets. Incubations were terminated by centrifugation at 1000 g.

Figure 1:
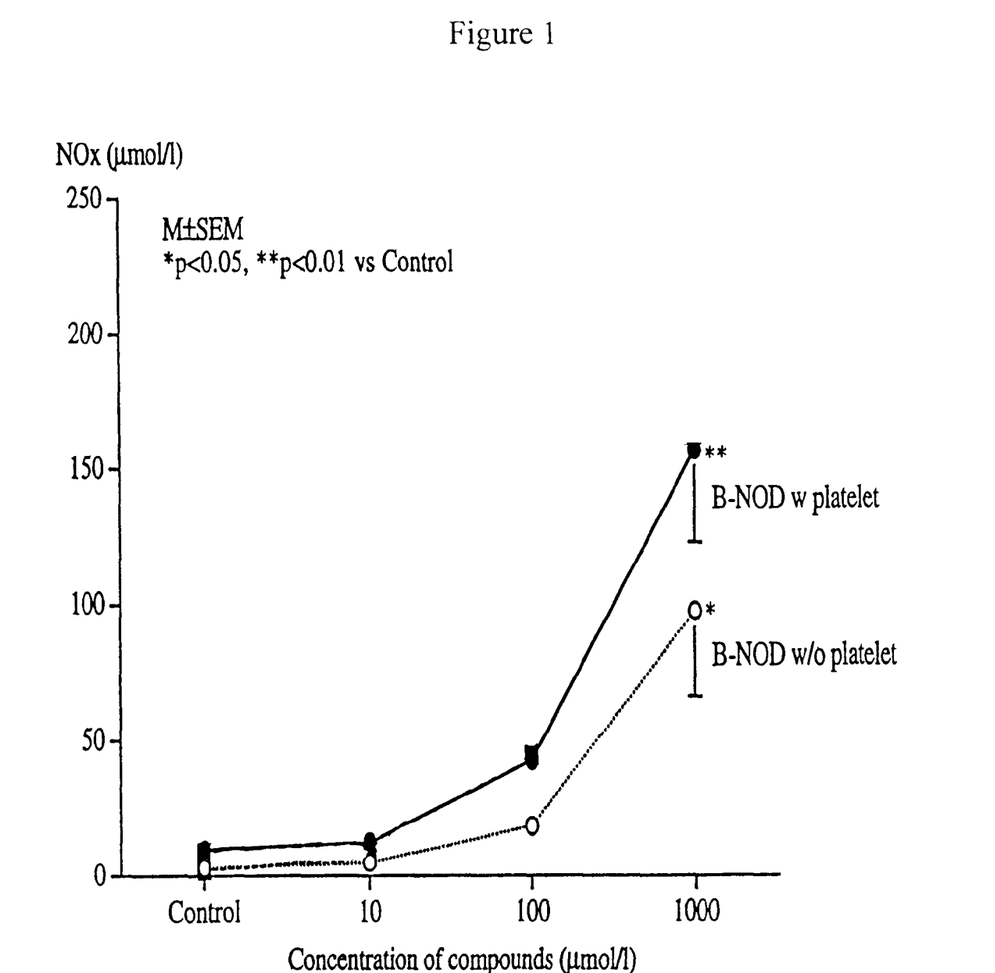
FIG. 1 is a graph showing the effect of B-NOD on $NO_x(NO_2$ and $NO_3)$ concentration with (closed circles) and without platelets (open circles). A dose-dependent increase in $NO_x$, the oxidation products of NO, is observed. X axis: Concentration of B-NOD (μmol/l); Y axis: Concentration of $NO_x$ (μmol/l).

NO production is shown in FIG. 1. In every case, B-NOD increased NO production in a dose-dependent manner. However, total release of NO was greater in the presence of platelets. The maximal NO release was 98 µmol/l without platelets and 156 µmol/l in the presence of platelets.

Example 2

Platelet cGMP In Vitro

Figure 2:
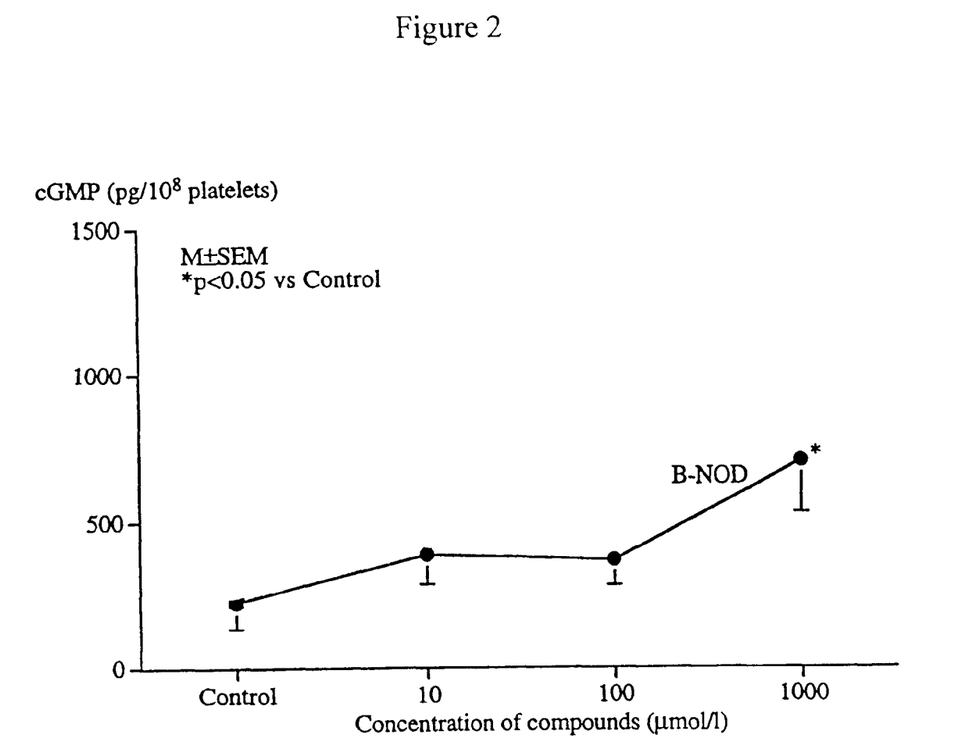
FIG. 2 is graph showing the effect of B-NOD on cGMP production in platelets. A dose-dependent increase in cGMP production is seen with B-NOD. X axis: Concentration of B-NOD (μmol/l); Y axis: Concentration of cGMP (pg/$10^8$ platelets).

Washed platelets were prepared from human blood as described above. 400 µl aliquots were incubated in the presence of B-NOD (10, 100 or 1000 µM) or methanol for 10 minutes. Incubations were terminated by centrifugation at 1000 g and the supernatant was removed. Ice-cold phosphate buffer was added to the pellets, and the pellets were sonicated for 20 seconds. cGMP was measured using an acetylation enzyme immunoassay system (Biotrak, Piscataway, N.J.). B-NOD increased cyclic GMP production in a dose-dependent manner, as shown in FIG. 2.

Example 3

Platelet Aggregation In Vitro

Healthy male New Zealand rabbits were anesthetized with pentobarbital (10 mg/kg iv), ketamine (40 mg/kg im), xylazine (10 mg/kg im) and atropine (0.5 mg im). They were incubated and mechanically ventilated with 95% oxygen (rate 40 strokes/min, tidal volume 25 ml). The heart was exposed with a median sternotomy, blood (40 ml) was collected from the right ventricle and washed platelets were prepared as described above. Platelet aggregation was monitored by a standard nephelometric technique in which 0.5 ml of platelet suspension ($2 \times 10^8$ platelets/ml) were incubated at 37° C. and stirred at 1000 rpm in an aggregometer (Model PAP-3, Bio/Data corporation, Horsham, Pa.). The antiaggregant effects of B-NOD (10, 100 or 1000 µM) were tested by incubating platelets with B-NOD at 37.8° C. before the addition of thrombin. Incubation was carried out for 10 min. Thrombin was used as an agonist at relatively low concentrations (0.04 to 0.14 U/ml) to obtain submaximal aggregation in order to evaluate the drug's inhibitory effect.

Figure 3:
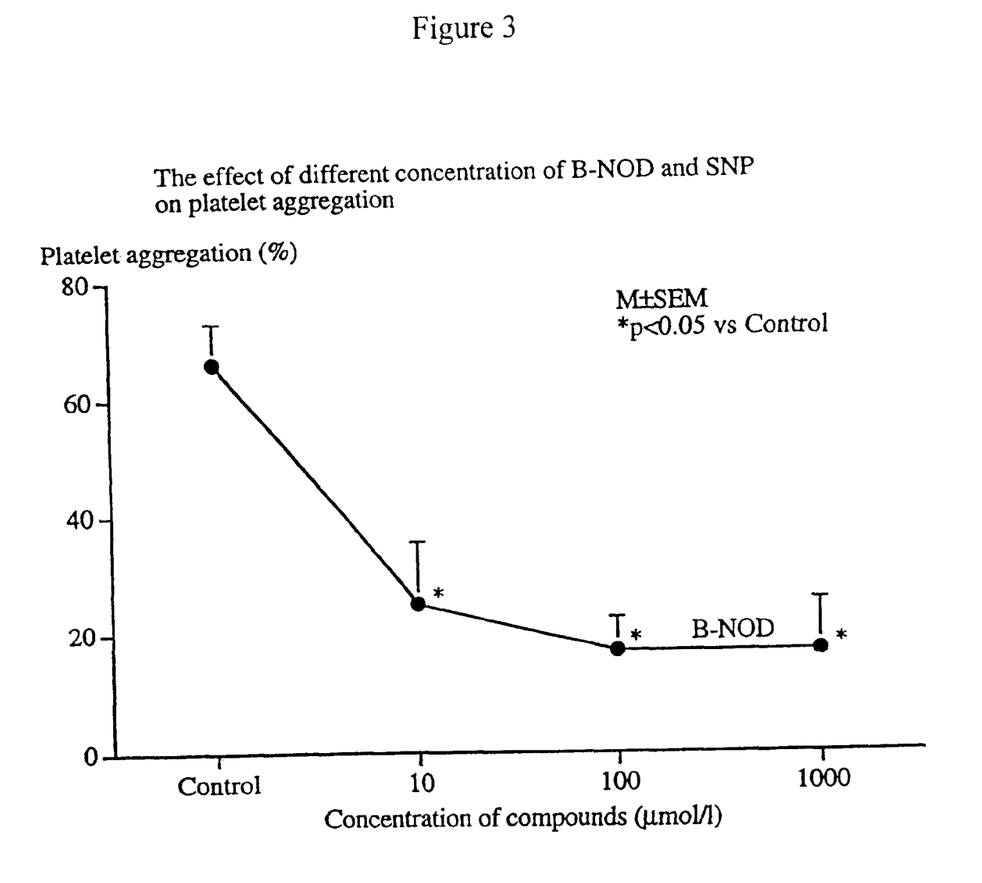
FIG. 3 is graph showing the effect of B-NOD concentration on platelet aggregation. Inhibition of aggregation is observed. X axis: Concentration of B-NOD (μmol/l); Y axis: percent platelet aggregation.

The effect of B-NOD on platelet aggregation is shown in FIG. 3. B-NOD inhibition of platelet aggregation was approximately 25% as compared to the control.

Example 4

Nitric Oxide Generation In Vivo

New Zealand White male rabbits were given 80 mg/kg of B-NOD. B-NOD was dissolved in 2 ml DMSO, suspended in 8 ml carboxymethylcellulose (0.5%) and administered orally. Blood (1 ml) was drawn from the ear vein using heparinized syringes before and 10 minutes, 30 minutes, 1 hour, 3 hours, 5 hours, 7 hours, and 24 hours following B-NOD administration. Blood samples were centrifuged at 1200 g for 10 minutes and deproteinized by an ultrafiltration device (MPS Micropartition, Millipore Corporation, Bedford, Mass.) and centrifuged again at 2500 g for 90 minutes. Plasma $NO_x$ was measured by chemiluminescence as described above.

Figure 4:
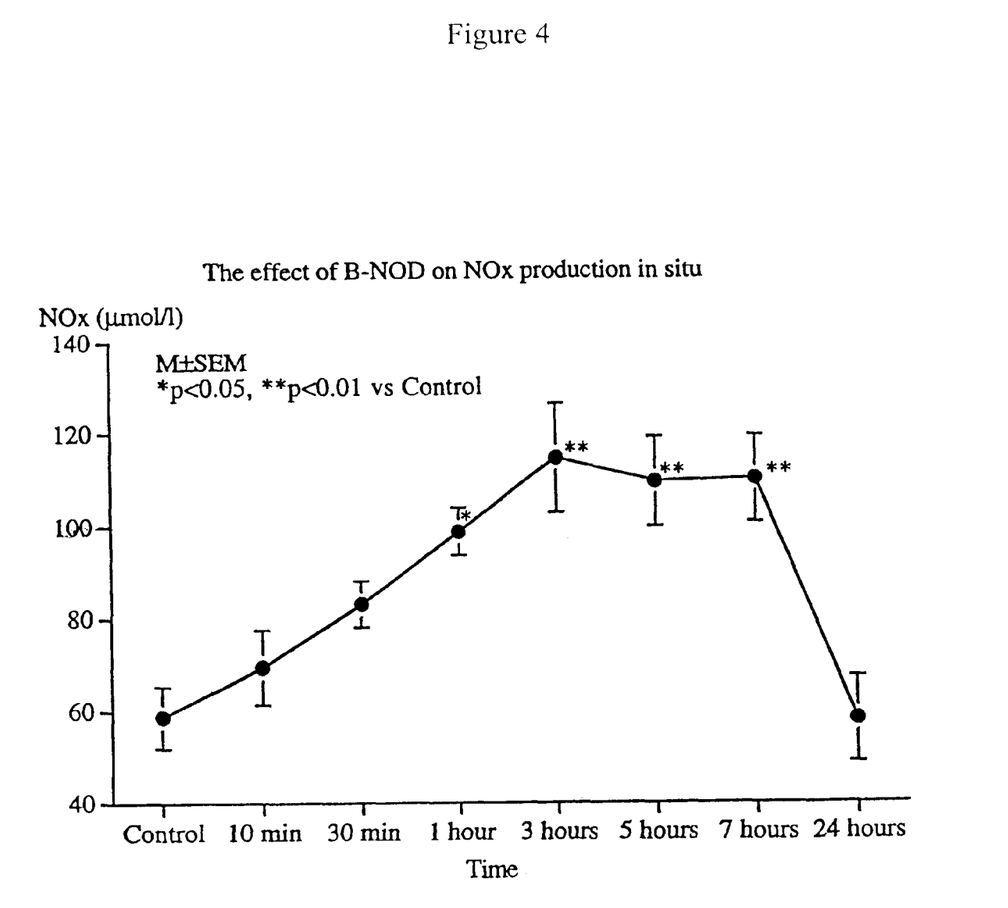
FIG. 4 is a graph showing the effect of B-NOD on $NO_x$ production in vivo. B-NOD was administered orally. A stepwise increase in $NO_x$ concentration in plasma with time was observed up to seven hours following administration of B-NOD. After 24 hours, the concentration of $NO_x$ had returned to the control level. X axis: Time; Y axis: $NO_x$ concentration (μmol/l).

Heart rate and systolic and diastolic blood pressures were measured through a 22 gauge by one inch catheter inserted into the ear artery connected to a DIGI-MED™ Heart Performance Analyzer 100 (Louisville, Ky.). Determination of blood pressure and heart rate were carried out prior to and 1, 3, 5 hours after B-NOD administration. FIG. 4 illustrates concentrations of $NO_x$ in plasma of animals up to 24 hours following administration of B-NOD. An increase in $NO_x$ concentration from 59 to 115 μmol/l was observed three hours following administration. Concentration of $NO_x$ then plateaued for seven hours following administration. After 24 hours, $NO_x$ values had returned to control values.

Example 5

Blood Pressure and Heart Rate

Figure 5:
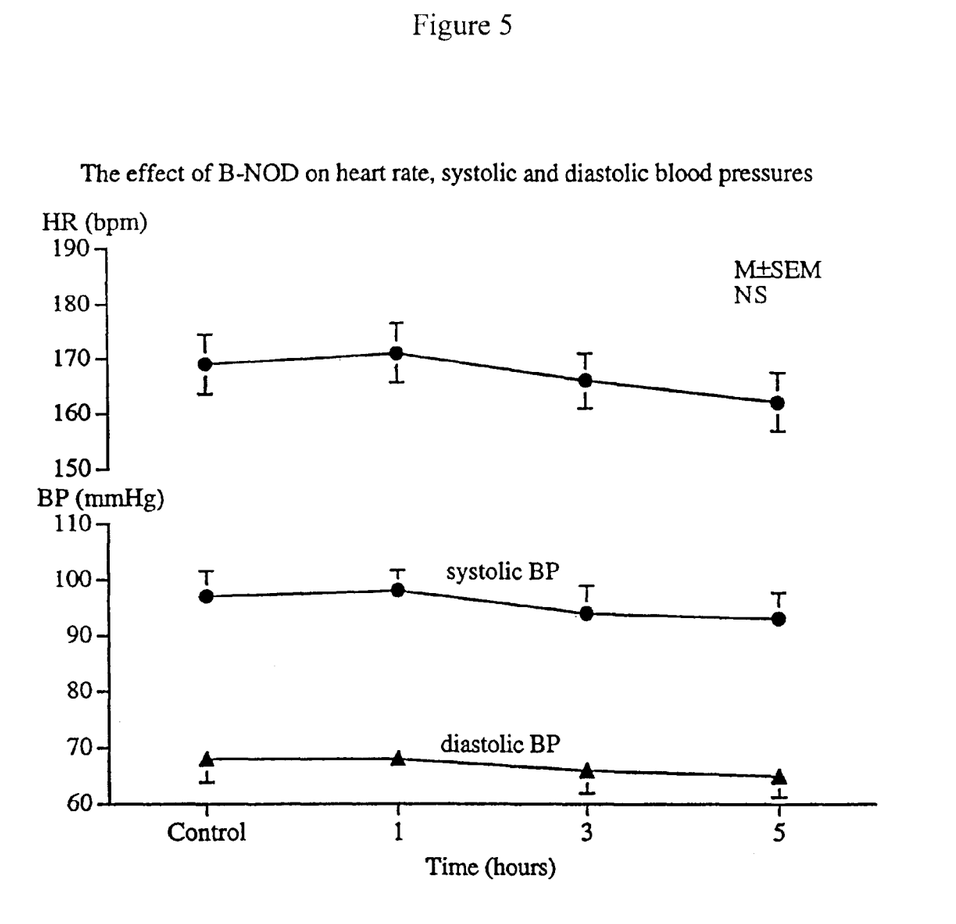
FIG. 5 is a graph showing the effect of B-NOD on heart rate and systolic and diastolic blood pressures up to five hours following administration of the compound. No changes are noted. X axis: Heart rate (bpm) or blood pressure (mm Hg); Y axis: Time (hours).

Several NO donors are known to cause a fall in blood pressure, particularly when administered intravenously. In contrast, B-NOD did not affect either systolic or diastolic pressures one, three and five hours following administration, shown in FIG. 5. Heart rate equally failed to change during this time frame.

The above descriptions of the effects of B-NOD are for illustrative purposes. Because of variations which will be apparent to those skilled in the art, the present invention is not intended to be limited to the particular embodiments described above. The scope of the invention is defined in the following claims.

What is claimed is:

1. A composition comprising a compound of the formula:

wherein R is $(CH_2)_n$, wherein n ranges from 1 to 8 and wherein each hydrogen atom on the alkylene group and on the phenyl groups can optionally be replaced by a substituent selected from the group consisting of alkyl, cycloalkyl, heterocycloalkyl, aryl, heteroaryl, halo, and hydroxy groups.

2. The composition according to claim 1, wherein n is 1.

3. The composition according to claim 1, wherein the compound is 1,3-(nitrooxymethyl)phenyl 2-hydroxybenzoate.

4. The composition according to claim 1, wherein at least one hydrogen atom on the alkylene group or on one of the phenyl groups is replaced by a substituent selected from the group consisting of alkyl, cycloalkyl, heterocycloalkyl, aryl, heteroaryl, halo, and hydroxy groups.

5. The composition according to claim 1, wherein none of the hydrogen atoms on the alkylene group and on the phenyl groups are replaced by a substituent.

6. The composition according to claim 5, wherein n is 1.

7. The composition according to claim 1, wherein the compound has the formula:

8. The composition according to claim 7, wherein n is 1.

9. The composition according to claim 7, wherein at least one hydrogen atom on the alkylene group or on one of the phenyl groups is replaced by a substituent selected from the group consisting of alkyl, cycloalkyl, heterocycloalkyl, aryl, heteroaryl, halo, and hydroxy groups.

10. The composition according to claim 7, wherein none of the hydrogen atoms on the alkylene group and on the phenyl groups are replaced by a substituent.

11. A method for treating coronary artery disease comprising administering a pharmaceutically-acceptable amount of a composition of claim 1 to a patient in need thereof.

12. The method according to claim 11, wherein the composition is administered in an amount ranging from about 1 to about 500 mg/kg/day.

13. The method according to claim 11, wherein the composition is administered in an amount ranging from about 5 to about 400 mg/kg/day.

14. The method according to claim 11, wherein the composition is administered in an amount ranging from about 100 to about 200 mg/kg/day.

15. The method according to claim 11, wherein the composition is administered following myocardial infarction.

16. The method according to claim 11, wherein in the compound n is 1.

17. The method according to claim 11, wherein in the compound at least one hydrogen atom on the alkylene group or on one of the phenyl groups is replaced by a substituent selected from the group consisting of alkyl, cycloalkyl, heterocycloalkyl, aryl, heteroaryl, halo, and hydroxy groups.

18. The method according to claim 11, wherein in the compound none of the hydrogen atoms on the alkylene group and on the phenyl groups are replaced by a substituent.

19. The method according to claim 18, wherein in the compound n is 1.

20. The method according to claim 11, wherein the compound has the formula:

21. The method according to claim 11, wherein the compound is 1,3-(nitrooxymethyl)phenyl 2-hydroxybenzoate.

22. The method according to claim 21, wherein the composition is administered in an amount ranging from about 100 to about 200 mg/kg/day.

23. A method of counteracting thromboxane, comprising administering a pharmaceutically-acceptable amount of a composition of claim 1 to a patient in need thereof.

24. A method of inhibiting platelet activation comprising administering a pharmaceutically-acceptable amount of a composition of claim 1 to a patient in need thereof.

25. A method of stimulating prostanoids through activation of cyclooxygenase comprising administering a pharmaceutically-acceptable amount of a composition of claim 1 to a patient in need thereof.

26. A method of reducing myocardial contractility comprising administering a pharmaceutically-acceptable amount of a composition of claim 1 to a patient in need thereof.

27. A method of attenuating inotropic response comprising administering a pharmaceutically-acceptable amount of a composition of claim 1 to a patient in need thereof.

28. A method of reducing cardiac lactate accumulation by forming cGMP comprising administering a pharmaceutically-acceptable amount of a composition of claim 1 to a patient in need thereof.

29. A method of dilating coronary arteries comprising administering a pharmaceutically-acceptable amount of a composition of claim 1 to a patient in need thereof.

30. A method of suppressing ventricular fibrillation comprising administering a pharmaceutically-acceptable amount of a composition of claim 1 to a patient in need thereof.

31. A method of treating or preventing strokes or embolism comprising administering a pharmaceutically-acceptable amount of a composition of claim 1 to a patient in need thereof.

32. The method according to claim 23, wherein the compound is 1,3-(nitrooxymethyl)phenyl 2-hydroxybenzoate.

33. The method according to claim 24, wherein the compound is 1,3-(nitrooxymethyl)phenyl 2-hydroxybenzoate.

34. The method according to claim 25, wherein the compound is 1,3-(nitrooxymethyl)phenyl 2-hydroxybenzoate.

35. The method according to claim 26, wherein the compound is 1,3-(nitrooxymethyl)phenyl 2-hydroxybenzoate.

36. The method according to claim 27, wherein the compound is 1,3-(nitrooxymethyl)phenyl 2-hydroxybenzoate.

37. The method according to claim 28, wherein the compound is 1,3-(nitrooxymethyl)phenyl 2-hydroxybenzoate.

38. The method according to claim 29, wherein the compound is 1,3-(nitrooxymethyl)phenyl 2-hydroxybenzoate.

39. The method according to claim 30, wherein the compound is 1,3-(nitrooxymethyl )phenyl 2-hydroxybenzoate.

40. The method according to claim 31, wherein the compound is 1,3-(nitrooxymethyl)phenyl 2-hydroxybenzoate.

* * * * *